United States Patent
Borman et al.

(10) Patent No.: US 6,444,477 B1
(45) Date of Patent: Sep. 3, 2002

(54) ASSAY METHOD FOR DETECTING 5-$HT_{2B}$ ANTAGONISTS

(75) Inventors: Richard A. Borman; Nicholas S. Tilford, both of Hertfordshire; Gordon S. Baxter, Cambridge, all of (GB)

(73) Assignee: Pharmagene Laboratories Limited, Hertfordshire (GB)

( * ) Notice: Subject to any disclaimer, the term of this patent is extended or adjusted under 35 U.S.C. 154(b) by 0 days.

(21) Appl. No.: 09/722,379

(22) Filed: Nov. 28, 2000

(51) Int. Cl.$^7$ ................... G01N 33/567; G01N 33/00; C07K 17/00
(52) U.S. Cl. ................ 436/503; 530/350; 435/7.1
(58) Field of Search ................ 530/350; 436/503, 436/501; 435/7.1, 7.2, 7.21

(56) References Cited

U.S. PATENT DOCUMENTS

| | | |
|---|---|---|
| 5,863,924 A | 1/1999 | Berger et al. |
| 5,952,331 A | 9/1999 | Berger et al. |
| 5,958,934 A | 9/1999 | Berger et al. |

FOREIGN PATENT DOCUMENTS

| | | |
|---|---|---|
| WO | WO 97/44326 | 11/1997 |
| WO | WO 01/08668 A2 | 2/2001 |

OTHER PUBLICATIONS

De Ponti, et al, 1998, Pharmacol. Ther., 80(1):49–88, esp. pp 53–60.*
Briejer, et al, 1995, Arch int. Pharmacodyn. 329: 121–133, esp. Fig.7.*
Read, et al, 1994, Pharmac. Ther. 62:159–173, esp Table 2 and p. 168.*
Borman, et al, 1996, Europ. J. Pharmacol, 309: 271–274.*
Mangel et al, "Review Article: the safety and efficacy of alosetron, a . . . ", Aliment Pharmacol Ther 1999; 13 (Suppl. 2): 77–82; XP–000980361.
Humphrey et al, "Review Article: the therapeutic potential of . . . ", Aliment Pharmacol Ther 1999; 13 (Suppl. 2): 31–38; XP–000980388.
Kishibayashi et al, "5–$HT_3$ Receptor Antagonists. 3. Quinoline . . . ", J. Med. Chem. 1993, 36, 3286–3292; XP–002158321.
Bonhaus et al, "RS–127445: a selective, high affinity, orally . . . ", British Journal of Pharmacology (1999) 127, 1075–1083; XP–000980373.

* cited by examiner

*Primary Examiner*—Elizabeth Kemmerer
*Assistant Examiner*—Sandra Wegert
(74) *Attorney, Agent, or Firm*—Nixon & Vanderhye P.C.

(57) ABSTRACT

The present invention relates to the finding that receptors for the neurotransmitter 5-HT of the 5-$HT_{2B}$ class are located on the human colon, and that their activation potentiates neuronally-mediated responses, and are thus causative in the abnormal motility and pain associated with IBS. The invention provides a method of treatment of IBS which comprises providing to a patient in need of treatment an effective amount of a 5HT2B receptor antagonist which acts on 5HT2B receptors located in the colon of said patient. Such antagonists may be administered in the form of compositions adapted to be delivered to the colon, such as depot formulations and suppositories. Assay methods for the development of compounds for the treatment of IBS are also provided.

3 Claims, 3 Drawing Sheets

Low power

ASSAY METHOD FOR DETECTING 5-HT$_{2B}$ ANTAGONISTS

IBS (irritable bowel syndrome) is a gastrointestinal disorder which is amongst the most commonly encountered in primary care. It is approximately twice as prevalent in women as it is in men and presents as a collection of symptoms which vary between patients and, within a single patient, over time. Symptoms always include lower abdominal pain which may be associated with constipation and/or diarrhoea.

Diagnosis of IBS is performed by excluding other diseases, followed by positive symptomatic diagnosis which is carried out according to the Manning or Rome criteria. A recent review by experts in the field has led to publication of revised diagnostic criteria (Rome 2), and updated diagnosis and treatment recommendations, based on research results. Recent approaches to the treatment of IBS have been based around the finding that levels of the neurotranmitter 5-hydroxytrptamine (5-HT) and it's metabolites are raised in the plasma of patients with IBS. 5-HT has a number of different receptor subtypes found in the human body.

Observations in animal studies have shown that both 5-HT$_3$ and 5-HT$_4$ receptors are present on myenteric neurones and mediate the release of excitatory neurotransmitters which cause contraction of gastrointestinal smooth muscle. This has led to the development of both 5-HT$_4$ agonists and antagonists, and 5-HT$_3$ antagonists. However, studies in man have not revealed the presence of either 5-HT$_4$ or 5-HT$_3$ receptors on myenteric neurones, so the specific receptors exerting neuronal control of gastrointestinal function are unknown.

The prior art has also speculated that a 5-HT$_{2B}$ antagonist may have use in the treatment of irritable bowel disorders these speculations are in the public domain. However, the basis for credible development of such an approach has not previously been determined. The supposition is based on observations in rat, where the receptor is present in the stomach fundus, and mediates contraction. Similarly, the authors of U.S. Pat. No. 5,457,101 (and later WO 96/24351 and WO 97/35578) base their proposal for the use of 5-HT$_{2B}$ antagonists on the observation of 5-HT$_{2B}$ mediated contraction of rat colon smooth muscle.

U.S. Pat. No. 5,952,331 also proposes a role for 5-HT in the pathology of IBS. However, the claim that 5-HT$_{2B}$ receptors might be beneficial in the treatment of IBS is based on three indirect observations:

5-HT$_{2B}$ receptors are present in human intestine. However, the two references cited in U.S. Pat. No. 5,952,331 report the presence of 5-HT$_{2B}$ receptors which contract small intestinal smooth muscle. There is no evidence, either experimental or clinical, that this mechanism of action has any relevance to IBS. In addition, there is no evidence that these actions in human intestinal tissue are accompanied by production of nitric oxide, leading to the sensitization of sensory nerve fibres.

Non-selective 5-HT$_{2B}$ receptor antagonists are clinically effective in reducing the pain associated with IBS. The first of these studies investigated the use of mianserin in the treatment of IBS and non-ulcer dyspepsia, and showed the treatment to offer alleviation of symptoms. Mianserin is a non-selective alpha-2 adrenoceptor, 5-HT1, 2 and 3, and histamine H1 and H2 receptor antagonist, and it's beneficial effects can not therefore be attributed solely to 5-HT$_{2B}$ receptor stimulation. In the second reference, the disease under investigation was "abdominal migraine" which shares little similarity to IBS. Entry criteria for the trial included at least bimonthly attacks, abdominal pain with facial pallor, and at least one first-degree (or two second degree) relatives with a history of migraine or recurrent headaches. These authors themselves stated that there is no reason to believe that the treatment [pizotifen] would be effective in patients with abdominal pain who did not meet these criteria, and it is therefore difficult to find evidence from this trial to support the use of pizotifen in IBS. In addition, pizotifen is a non-selective 5-HT$_2$ receptor, which is non-surmountable at 5-HT$_{2A}$ receptors (Prins et al., 1997), and additionally shows significant affinity for 5-HT$_3$ receptors (Schmidt & Peroutka, 1989). The evidence (from these clinical studies) to support the use of 5-HT$_{2B}$ receptor antagonists in IBS is therefore not credible.

These separate and independent pieces of evidence are claimed as support for the use of 5-HT$_{2B}$ receptor antagonists in the treatment of IBS. However, U.S. Pat. No. 5,952,331 provides no experimental evidence to support this claim.

DISCLOSURE OF THE INVENTION

The present inventors have investigated the location and action of 5-HT$_{2B}$ receptors in human colon tissue. The inventors have demonstrated, however, that 5-HT$_{2B}$ receptors in human colon have no significant effect on basal tone in human colon (i.e. no effect on resting colon), but that their activation potentiates contractile responses to neuronal stimulation. In other words, it is believed that in the human colon, 5-HT acts on 5-HT$_{2B}$ receptors to make the colon hypersenstive to neuronally-mediated stimulation. It is this mechanism which it is believed to be the key to the involvement of 5-HT$_{2B}$ receptors in the pathogenesis of IBS, rather than merely by causing direct smooth muscle contraction.

Thus for the first time, it is shown herein that 5-HT$_{2B}$ receptors are present on both nerves and smooth muscle of human colon, and that their activation potentiates neuronally-mediated responses, and are thus causative in the abnormal motility and pain associated with IBS. For this reason, there is provided direct experimental evidence that 5-HT$_{2B}$ receptors will be useful in the treatment of IBS.

The demonstration of 5-HT$_{2B}$ receptors localised on neuronal elements within the human GI tract is not in the public domain, nor is the potentiation of neuronally-induced contractions induced by activation of 5-HT$_{2B}$ receptors. Thus the present findings allow the development of a rational approach to the development of an IBS treatment.

The present invention thus provides, for the first time, a rational approach to the treatment of IBS via 5HT2B antagonists, as well as a novel means for the development of novel compounds useful in the treatment of IBS.

In a first aspect, the invention provides for a method of treatment of IBS which comprises providing to a patient in need of treatment an effective amount of a 5HT2B receptor antagonist which acts on 5HT2B receptors located in the colon of said patient.

Alternatively, the invention provides the use of a 5HT2B receptor antagonist for the manufacture of a medicament which acts upon 5HT2B receptors of the colon for the treatment of ISS.

In a further aspect, the invention provides a composition comprising a 5HT2B receptor antagonist adapted for administration to a human subject such that the antagonist is released in the colon. Such compositions included delayed release formulations, taken orally, as well as compositions adapted to be delivered to the colon, such as depot formulations and suppositories.

In another embodiment, the present findings provide a novel means in the development of compounds for use in the treatment of GI disorders, the means being the use of human colon smooth muscle preparation as an assay for the detection of compounds which may be beneficial in the treatment of GI disorder, and particularly IBS. The colon smooth muscle preparation may be used in an assay in which it is electrically-stimulated, so as to contract in the presence of such stimulation, and compounds assayed for the ability to inhibit 5-HT-induced potentiation of such contraction. Such an assay provides a means of detecting compounds with 5-HT2B activity.

DETAILED DESCRIPTION OF THE INVENTION

$5\text{-}HT_{2B}$ Receptor Antagonist

Figure 1:
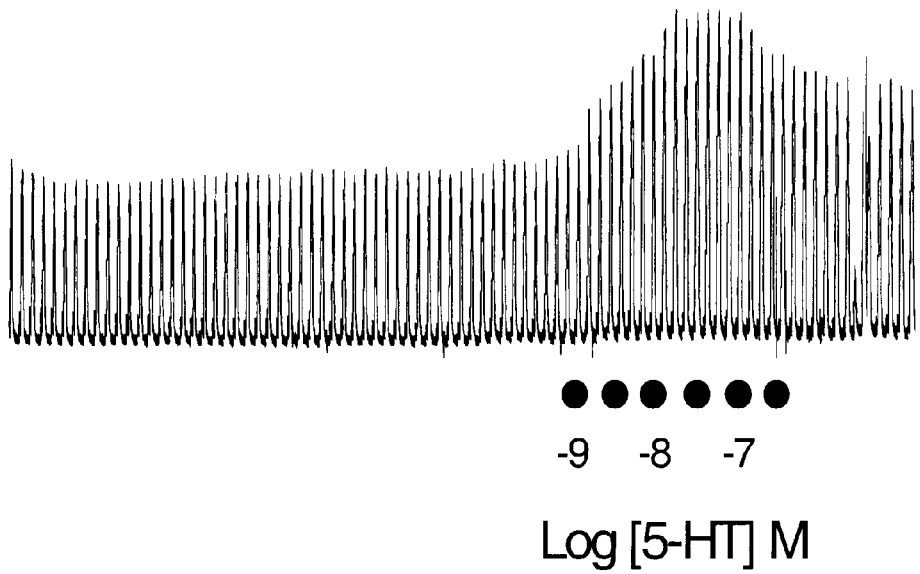
FIG. 1 shows Effect of 5-HT on electrically-induced contractions of longitudinal muscle strips from human colon. The transient contractile response to ENS, and the potent potentiation of this neurally-mediated response by increasing concentrations of 5-HT (−9 to−5M) is illustrated.

A large number of $5\text{-}HT_{2B}$ receptor antagonists are known per se in the art. These include spiroterahydro-beta-carboline derivatives (eg as described in WO97/35578), aryl pyrimidine derivatives (eg WO97/44326), indole derivatives (WO94/25012, WO96/23783, WO97/37989, WO97/08167, WO96/11929, WO96/23769), fused indoles (WO96/24351), heterocyclic urea derivatives (WO94/14801, WO96/11930, WO92/05170), condensed indole derivatives (WO94/04533, WO95/21844), benzocondensed five membered heterocycle carboxamides (WO96/02537), tricyclic derivatives (WO95/29177), thieno-indole derivatives (WO94/22871), indoline derivatives (WO95/01976), carboline derivatives (EP-A-0620222) and benzodiazepines (U.S. Pat. No. 5,457,101). The disclosures of such compounds are incorporated herein by reference. These compounds may be used in the present invention.

In a preferred aspect, the $5\text{-}HT_{2B}$ receptor antagonist is a selective $5\text{-}HT_{2B}$ receptor antagonist. Selective means fulfilling one or more of the following parameters:

1. Affinity ($K_D$) at the human $5\text{-}HT_{2B}$ receptor (measured at the cloned human receptor transfected in a mammalian cell line) $\geq 7.0$, more preferably $\geq 8$.
2. Antagonist potency ($pK_B$ at the human $5\text{-}HT_{2B}$ receptor in colon $\geq 7.0$ more preferably $\geq 8$.
3. Ratio of binding at the $5\text{-}HT_{2B}$ vs $5\text{-}HT_{2C}$ receptor (measured at the cloned human receptors transfected in a mammalian cell line) $\geq 10$, more preferably $\geq 100$.
4. Ratio of binding over other members of 5-HT family of (measured at the cloned human receptors transfected in a mammalian cell line) $\geq 30$, more preferably $\geq 100$.
5. MW of compound $\leq 500$.

The values $K_D$ and $pK_B$ may be determined as described below herein below. Criteria 1–4 are expressed without an upper limit, since the skilled person will appreciate that it is not conventional when defining criteria of this type to do so. However, in practice compounds which fulfil these criteria will be in a range which is from the specified values to 3–4 log higher (e.g. for (1) above from $\geq 7.0$ to 10.0 to 11.0.

Preferably, compounds meet at least two, preferably at least three of the above criteria. For example, compounds which meet criteria 1+2, 1+3, 1+4, 1+5, 2+3, 2+4, 2+5 are preferred groups of two criteria. Groups of three criteria include 1+2+3, 1+2+4, 1+2+5, 2+3+4, 1+3+4, 2+3+5, 3+4+5 and the like. Compounds which meet one of more of the above criteria and which may be absorbed orally with no significant effect on hepatocyte function and of low or non-toxicity are particularly preferred.

Specific compounds useful in the practice of the present invention include:

RS-127445 (2-amino-4-(4-fluoronaphth-1-yl)-6-isopropylpyrimidine) or a salt or N-oxide thereof;

LY-23728 (N-(1-methyl-1H-indol-5-yl)N'-(-bezyl)-2,3,4, 9-tetrahydro-1H-beta-carboline). This has a 100-fold selectivity for $5\text{-}HT_{2B}$ over $5\text{-}HT_{2C}$ and $5\text{-}MT_{2A}$. It has not been tested in the prior art in human colon.;

SB-204741 (N-(1-methyl-5-indolyl)-N'-(3-methyl-5-isothiazolyl) urea). Active in colon, potency of 6.8, at least 10-fold selectivity over other 5-RT2 receptors;

SB-200646 (N-(1-methyl-5-indolyl)-N'-(3-pyridyl)urea hydrochloride). Non-selective $5\text{-}HT_{2B}/2C$ receptor antagonist;

SB-206553 (5-methyl-1-(3-pyridylcarbamoyl)-1,2,3,5-tetrahydropyrrolo[2,3-f]indole). This is a non-selective $5\text{-}HT_{2B}/2C$ receptor antagonist with >100-fold selectivity over $5\text{-}HT_{2A}$ receptors and is a potent antagonist of 5-HT response in human colon (8.5); and SB-215505 (6-chloro-5-methyl-N-(5-quinolyl)-2,3-dihydro-1H-indole-1-carboxamide). Potent, selective $5\text{-}HT_{2B}$ receptor antagonist, potency of 9.9 and 100-fold selectivity over $5\text{-}HT_{2A}$ and $5\text{-}HT_{2C}$ receptors.

Effective Amount

It will be appreciated that the precise therapeutic dose of a $5\text{-}HT_{2A}$ receptor antagonist, expressed in the form of its free bas will depend on the age and condition of the patient and the nature of the IBS to be treated, and the affinity of the $5\text{-}HT_{2B}$ receptor antagonist for the human $5\text{-}HT_{2B}$ receptor, and will be at the discretion of the attendant physician.

However, in general, effective doses for the treatment of IBS patients will lie in the range of 0.001 to 1000 mg, such as 0.01 to 500 mg, preferably 0.1 to 250 mg, for example 0.5, 10, 20, or 50 mg of a $5\text{-}HT_{2B}$ receptor antagonist per unit dose, which could be administered in single or divided doses, for example 1 to 4 times per day.

Compositions

The $5\text{-}HT_{2B}$ receptor antagonist, or a pharmaceutically acceptable derivative thereof, may be formulated in conventional manner using one or more acceptable carriers or excipients. Thus a 5- $HT_{2B}$ receptor antagonist, or a pharmaceutically acceptable derivative thereof, may for example be formulated for oral, sub-lingual, buccal, parenteral, rectal or intranasal administration, or in a form suitable for administration by inhalation or insufflation (either through the nose or mouth), or in a form suitable for topical administration.

For oral administration the pharmaceutical compositions may take the form of, for example, tablets or capsules prepared by conventional means with pharmaceutically acceptable excipients such as binding agents (eg pregelatinised maize starch, polyvinylpyrrolidone or hydroxypropyl methylcellulose); filters (eg lactose, microcrystalline cellulose or calcium phosphate); lubricants (eg magnesium stearate, talc or silica); disintegrates (eg potato starch or sodium starch glycollate); or wetting agents (eg sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (eg sorbitol syrup, methyl cellulose or hydrogenated edible fats); emulsifying agents (eg lecithin or acacia); non-aqueous vehicles (eg almond oil, oily esters or ethyl alcohol); and preservatives (eg methyl or propyl-p-hydroxybenzoates or sorbic acid).

For buccal administration the compositions may take the form of tablets or lozenges formulated in conventional manner.

For parenteral administration the compositions may take the form of injections, conveniently intravenous, intramuscular or subcutaneous injections, for example bolus injections or continuous intravenous infusions. Formulations for injection may be presented in unit dosage form eg in ampoules or in multi-dose containers, optionally with an added preservative.

The compositions for parenteral administration may take such forms as suspensions, solutions or emulsions in oily or aqueous vehicles, and may contain formulatory agents such as suspending, stabilizing and/or dispersing agents. Alternatively, the compositions may be in dry form such as a powder, crystalline or freeze-dried solid for constitution with a suitable vehicle, eg sterile pyrogen-free water or isotonic saline before use. They may be presented, for example, in sterile ampoules or vials.

Tablets for sub-lingual administration may be formulated in a conventional manner.

For intranasal administration, or administration by inhalation or insufflation, conventional formulations may be employed. For topical administration the pharmaceutical compositions may be liquids, for example solutions, suspensions or emulsions presented in the form of creams or gels.

Compositions may also be formulated as depot preparations or delayed release formulations. Depot preparations may be administered by implantation (for example subcutaneously, transcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

Compositions adapted for release of the 5-HT$_{2B}$ receptor antagonist in the colon may be used. These include compositions in theform of suppositories or retention enemas for rectal administration.

Other such compositions included delayed release formulations, in which the 5-HT$_{2B}$ receptor antagonist is formulated in a manner which allows specific delivery to the small and large intestine, and more preferably specifically to the colon. This can be achieved by using delayed release formulations which are taken orally.

There are numerous teachings in the art of means to provide delayed release formulations of compounds such that the active ingredient is released primarily in the colon. Generally, such means provide for protection of the active ingredient from the environment of the stomach and intestines by means of one or more coatings. For example, EP-00572942, the disclosure of which is incorporated herein by reference, describes a delayed release composition comprising a core of active ingredient optionally combined with one or more excipientsi coated with an intermediate layer which delays release of the ingredient independently of pH, and an outer layer which dissolved in a pH dependent manner.

The outer layer may be a polymer such as cellulose acetophthalate, cellulose acetate terephthalate, cellulose acetate trimellitate, hydroxypropyl-methyl cellulose phthalate, polyvinyl alcohol phthalate, polyacrylate or a polymethacrylate. The coating will have little or no solubility at a pH lower than 5, but will dissolve at a more neutral or alkaline pH, for example of 7.5 or above. This coating protects the active ingredient during its passage through the stomach and intestines.

The intermediate layer will be a material such as a hydrophobic gelling polymer such as methylcellulose, carboxymethylcellulose, hydroxypropylmethylcellulose, polyvinyl alcohols, polysaccharides and the like.

An alternative approach is described in WO-09107949, which also uses two protecting layers. In this reference, the intermediate layer is an amorphous amylose, such as glassy or rubbery amylose. This layer is broken down by the action of enzymes of the microflora which are found in the colon. An outer layer of a film forming cellulose material or acrylic polymer material is then added to provide protection to the amylose layer. This outer layer dissolves in a pH-independent manner. The amylose is preferably glassy amylose with a glass transition temperature, Tg, of no less than 17° C., preferably no less than 30° C., and a molecular weight of at least 20,000, e.g. at least 100,000 daltons.

The film forming cellulose may be, for example, sodium carboxymethyl cellulose, sodiumcarboxymethyl 1-hydroxyethyl cellulose, 2-hydroxycellulose, 2-hydroxypropyl cellulose, methyl cellulose, and the like, preferably with a molecular weight range of from 42,0000 to 280,000 daltons. Acrylic polymer materials include acrylate and methacrylate polymers and copolymers thereof, preferably in the molecular weight range of from 15,000 to 250,000 daltons.

According to WO91/07949, the disclosure of which is incorporated herein by reference, the amylose coating may be from 5 to 50 $\mu$M in thickness around a core of active ingredient of, for example a 1 mm sphere, and the outer coating may also be of a similar size range. Coatings comprising a mixture of the amylose and film forming material are also described.

Delayed release compositions of the invention, including those as described above, will allow the substantial bulk of the active ingredient (for example at least 50% of each unit dosage form) released in the body of a subject to be released in the colon.

For example, a delayed release composition will show less than 20%, preferably less than 10% release of active ingredient after 3 hours in 0.1N HCl at 20° C., but more than 50%, preferably more than 75% release of active ingredient within 24 hours when at a pR of 7.0 or above (e.g. 7.5) and/or exposed to anaerobic microbial digestion by faecal microflora (for example using digestive conditions described in Example 4(d) of WO91/07949).

Assay Methods

The invention also provides a means to assay and verify the effectiveness of compounds as candidates for the treatment of IBS.

The assay of the invention comprises providing a section of human colon;

placing said section under tension;

electrically stimulating said section in the presence of a potential 5-HT$_{2B}$ receptor antagonist; and observing whether said potential 5-HT$_{2B}$ receptor antagonist is capable of antagonising the 5-HT induced potentiation of electrically stimulated contractions of said human colon.

The section of human colon will be from fresh tissue, for example recovered from patients undergoing surgery. The section is provided in a manner in which it can be conveniently placed under tension in suitable apparatus for the purposes of the assay. For example, a longitudinal section comprising muscle strips of the human colon may be used, as described in the accompanying examples.

In the accompanying examples, the strips of colon are about 2 mm wide by 20 mm long, so that they fit the apparatus used by the present inventors. The size of the strips may be varied according to experimental preference.

The strips may be placed in an oxygenated chamber containing a physiologically balanced salt solution, such as the Kreb's solution described in the accompanying examples. The strips of tissue are then placed under a tension (for example between hooks or other attachment means) and left to equilibrate. A tension of from 5 to 25, such as 10 to 15 mN is suitable, but may be varied according to the particular apparatus used. Once the tissue has equilibrated, it may be used to assay potential 5-HT$_{2B}$ receptor antagonists.

In the assay, the colon tissue is stimulated by electrical pulses (for example a 10 second pulse every 60 seconds) so that contraction of the tissue is observed upon pulsing, and relaxation of the tissue back to the resting tension is achieved between pulses. Under these conditions, we have observed that upon increasing concentrations of 5-HT, the contraction is markedly increased, though the basal level without stimulation is unaffected—see FIG. 1.

Compounds which are being assayed will be provided to the tissue at a range of concentrations (for example from $10^{-6}$M to $10^{-10}$M, preferably from $10^{-7}$M to $10^{-9}$M) and their ability to inhibit the 5-HT-induced EFS contractions determined. Compounds which have this ability will produce a rightward shift in the response curve of the type shown in FIG. 2.

The alteration in the response curve can be calculated by a standard method, according to the method of Arunlakshana, A. & Schild, H. O. ((1959). Some quantitative uses of drug antagonists. Br. J. Pharmacol. Chemother., 14, 48–58). This is a well known piece of work, which details the classical Schild Equation, providing the pK$_B$. The equation is:

$$pK_B = \log(\text{concentration ratio} - 1) - \log(\text{antagonist concentration}),$$

where the concentration ratio is the concentration of agonist producing a defined response (such as 50% of the maximum) in the presence of an antagonist, divided by the concentration producing the same response in the absence of antagonist, and the antagonist concentration is the concentration of antagonist producing that displacement in the agonist response.

The binding affinity, K$_D$, may be calculated by standard methods, for example by reference to Kenakin, T, ((1993), Pharmacologic analysis of drug-receptor interaction, 2$^{nd}$ Edition, Raven Press).

Compounds which demonstrate antagonism may be selected as candidates for the treatment of IBS.

The compounds which may be used in the assay of the invention include compounds which have been proposed in the art as having 5-HT receptor binding activity, particularly 5-HT$_{2B}$ receptor binding activity, but whose activity in colon tissue in particular has not been investigated. In such circumstances, the assay of the invention provides a validation means in the development of IBS therapies.

Furthermore, the assay provides a means for the testing and developments of compounds whose 5-HT$_{2B}$ activity is unknown, including novel compounds produced as part of a drug development program. Libraries of compounds are commercially available from a variety of sources and these may be used in the assay of the present invention.

Compounds which show antagonism at the 5-HT$_{2B}$ receptors in colon tissue may be formulated and used in accordance with the other aspects of the invention described herein, and such compounds and their use form a further aspect of the invention.

The following Examples illustrate the invention.

Gene Expression Data

The present applicants have developed protocols for quantitative analysis of mRNA expression using the ABI prism 7700 Sequence Detection System (Perkin Elmer). The system uses fluorogenic PROBES to generate sequence specific fluorescent signals during PCR. The probes are oligonucleotides with fluorescent reporter and quencher dyes attached. While a probe is intact, the intensity of reporter fluorescence is suppressed by a quencher. When a probe forms part of a replication complex during the PCR process, the quencher is separated from the reporter dye resulting in an increase in fluorescence which is then picked up by the 7700 sequence detector.

The ABI 7700 has a built in thermal cycler, and a laser directed at each of the 96 sample wells via bidirectional fibre optic cables. Emitted fluorescence travels through the cables to a detector where emissions which fall between 520 nm and 660 nm are collected every few seconds. The system software analyses the contribution of each component dye to the experimental spectrum, and normalises the signal to an internal reference dye. The peaks of these normalised 'reporter' values (Rn) are then plotted against thermal cycle number to produce an amplification plot—to allow visualisation of the extent of FCR product generation.

The starting copy number of a target sequence (Cn) is established by determining the fractional FCR cycle number (Ct) at which a PCR product is first detected—the point at which the fluorescence signal passes above a threshold baseline. Quantification of the amount of target mRNA in each sample is established through comparison of experimental Ct values with standard curves for the target sequence which are constructed during each experiment.

Human RNA

Total RNA was isolated from 72 human tissue samples, each from three different donors. Samples of RNA were used in this study only if intact 18s and 28s ribosomal RNA were detected by gel electrophoresis, if actin mRNA could be detected using the ABI 7700 sequence detector, and if genomic DNA formed less than 10% of the total nucleic acid sample. Total RNA samples were annealed to PGN-826R plus a GAPDH primer and reverse transcribed using MULV reverse transcriptase. Quantitative sequence detection was carried out on the resulting cDNA.

A DNase treatment step is carried out on all RNA samples prior to mapping, the effectiveness of the treatment is monitored for each set of map samples by running a control PCR plate which does not undergo the reverse transcription step.

RNA Integrity

A primer/probe set has been designed to span an intron/exon boundary in the sequence of the ubiquitously expressed GAPDH gene. The probe in this reagent set is labelled with a fluorophore which is spectrally distinct from that attached to the specific probe for the target of interest. A determination of the presence of GAPDH mRNA can therefore be carried out in the same well as that used to examine the copy number of the target of interest. Absence of a GAPDH signal within a well indicates that the RNA within that sample has been degraded.

Primer Probe Design

Primer/probe sets for detection of $5\text{-}HT_{2B}$ mRNA were designed by the applicants and positioned to amplify target sequences encoding amino acids in the intracellular loop between putative transmembrane domains V and VI. Off-line homology searches revealed no significant matches with gene sequences logged at Genbank.

The structure of the PRIMER/PROBE set used to amplify the $5\text{-}HT_{2B}$ receptor was as follows:

Forward Primer: PGN-826F
  5'-ACGCCTAACATGGTTGACTGTGTC-3'(SEQ ID NO:1)
Reverse Primer: PGN-1024R
  5'-TGAGGCTCTCTGTTCGTTGGAA -3'(SEQ ID NO:2)
Taqman Probe: PGN-894T
  5'-AGGTGGCAATGCTGGATGGTTCTCGA -3'(SEQ ID NO:3)

Primer/Probe Optimisation

Reaction conditions were optimised using genomic DNA as a template and a primer concentration grid followed by a probe concentration gradient experiment. Primer concentrations were selected to give the most efficient amplification of gene product i.e. those which generated a low threshold cycle and a relatively high accumulation of fluorescence (300 nM forward, 50 nM reverse). These optimal primer concentrations were then used to select the optimum probe concentration. A probe concentration of 200 nM gave the maximum fluorescent signal and minimum threshold cycle value.

Results

Of the 72 tissues taken from the 3 donors tested, mRNA for the human $5\text{-}HT_{2B}$ receptor was found in at least one donor of all tissues tested, showing that the receptor gene is ubiquitously expressed. Expression was found to be highest in the reproductive system, with particularly high expression being seen in uterus. Expression of $5\text{-}HT_{2B}$ receptor RNA was also high in all regions of the alimentary tract. In addition, high levels of 5-HT were found in liver parenchyma, kidney medulla, and the adrenal and thyroid glands.

In the alimentary system, $5\text{-}HT_{2B}$ receptor expression was found in all regions of the gastrointestinal tract. In colon smooth muscle, there was a large degree of variation in the levels of $5\text{-}HT_{2B}$ receptor mRNA between the three donors tested, with values ranging from 10 to approximately 13,000 copies of mRNA per 100 ng protein. There is no obvious reason for this high degree of variance: the levels of GAPDH was relatively comparable between the three donors. In summary, MRNA for the human $5\text{-}HT_{2B}$ receptor is expressed in all tissues tested. Particularly high levels were found in the GI tract, and in particular oesophagus and colon.

Immunocytochemistry

A monoclonal anti-$5\text{-}HT_{2B}$ receptor antibody was purchased from Pharmingen, Inc, USA (Catalog Number 60531A, Lot no. M017437). The antibody was raised against a recombinant fusion protein between glutathione-S transferase and the human $5\text{-}HT_{2B}$ receptor. The antibody has been shown to recognise both the immunogen and rat $5\text{-}HT_{2B}$ receptor.

Preparation of Human Tissue Extracts

Snap frozen human tissue (approx. 1 g) was added to 10 volumes of ice-cold 50 mM HEPES (pH 7.4), 1 mM EDTA, 1 mM EGTA, 250 mM sucrose, 0.2 mM PMSF. The tissue was homogenised using an Ultra-Turrax homogeniser on full speed for approx. 10 seconds. Sodium dodecyl sulphate (SDS) was added at a final concentration of 1%, for 10 min at room temperature, to solubilise proteins. Insoluble material was removed by centrifugation at 1,000×g for 10 min at room temperature. The supernatant was decanted and re-centrifuged 40,000×g for 15 min at room temperature. Protein was determined by the BCA method using BSA as a standard. The final protein extracts were stored at −20° C until use.

Dot-blotting of $5\text{-}HT_{2B}$-like Receptor Protein

The level of $5\text{-}HT_{2B}$-like receptor protein expression was determined in protein extracts of 82 human tissues and 2 stable human cell lines (HEK293 and 132N1). In brief, protein extracts were diluted to 0.4 mg protein/ml in 62.5 mM Tris-HCl (pH 6.8); 1% (w/v) SDS. Immunoblotting was performed using a 96-well perspex blotting manifold (Life Technologies). Before use, the manifold was washed in detergent, and rinsed in distilled water. A nitrocellulose sheet, pre-soaked with distilled water and a buffer containg 25 mM Tris (pH 8.3), 192 mM glycine, 20% methanol, was loaded into the manifold and claamped in placed by vacuum pressure. No sample vacuum was applied. Protein samples (100 μl/well) were added to wells and incubated for 1 hour at room temperature.

The resultant protein blot was removed from the manifold and rinsed in phosphate-buffered saline (PBS) for 5 min. The blot was stained with Ponceau S for 15 min to visualise the protein bound and to inactivate endogenous alkaline phosphatase enzyme. Destaining was achieved using PBS before blocking in PBS containing 1% (w/v) Marvel, 1% (w/v) BSA, 1% (v/v) sheep serum for 1 hour at room temperature. Anti-$5\text{-}HT_{2B}$ antibody diluted to 0.1 Ag/ml in PBS, 1% Marvel, 0.25% BSA (reagent dilutent) was added to the blot and incubated for 90 min at 37° C. After thorough washing, bound antibody was localised using an anti-mouse fluorescein-linked secondary antibody (1:600) (Amersham) and an anti-fluorescein alkaline phosphatase conjugate (diluted in 1:2500 in Tris-buffered saline, 1% Marvel, 0.25% BSA). Finally, bound conjugate was localised using enhanced chemifluorescence and imaged using a fluorimager (STORM Molecular Dynamics). The resultant image was quantified using ImageQuant software. Control values obtained using non-irmune mouse IgG1 as the primary antibody were subtracted from the results for the anti-5-$HT_{2B}$ antibody to correct for endogenous fluorescence or residual alkaline phosphatase activity in protein extracts.

Sodium Dodecyl Sulphate Polyacrylamide Gel Electrophoresis (SDS PAGE)

SDS PAGE was performed according to a modified method of Laemmli (1970). Samples for electrophoresis were solubilised in SDS sample buffer (25 mM Tris-HCl (pH 6.5), 4% (w/v) SOS, 10% (v/v) lycerol, 5% (v/v) β-mercaptoethanol, 0.001% (w/v) bromophenol Blue) and incubated for 1h at room temperature, Electrophoresis was performed in a vertical gel apparatus (Flowgen) equipped with 12×10 cm plates. Samples (40 µg protein) were resolved using a 4% stacking gel and a 7.5% resolving gel at a constant voltage of 200 V.

Western Blotting of Pesolved Proteins

Following SDS PAGE, resolved proteins were transferred to a 0.2 µm nitrocellulose membrane (Flowgen) according to Towbin et al. (1979) using a mini-blotting tank (Flowgen). Efficient transfer was achieved at 100 V for 1 hour in 25 mM Tris-HCl (pH 8.3), 192 mM glycine, 20% methanol, 0.1% SDS. 5-$HT_{2B}$-like receptor protein was localised using a selective antibody as detailed in section 2.2.2. molecular weights of proteins were determined from FITC-labelled marker proteins (Sigma) using Fragment Analysis software (Molecular Dynamics).

Immunocytochemistry

Fresh frozen (10 mm) or formalin-fixed paraffin-embedded (5–7 mm) sections of human tissue including colon and ileum, were mounted onto silane-coated slides. Frozen sections were stored at −80° C. until use, while paraffin-embedded sections were stored at room temperature (RT).

Frozen sections were brought to RT and air-dried for 1 hr, when required. These sections were then fixed in acetone for 30 min and air-dried for 1 h. Paraffin-embedded sections were rehydrated in graded alcohol. Endogenous peroxidase activity in frozen and paraffin-embedded sections was quenched by incubation in either 1% $H_2O_2$/0.1% $NaN_3$ in PBS for frozen sections, or 3% $H_2O_2$ in distilled water for paraffin-embedded sections (30 min). (All incubations and washes were carried out on an orbital shaker at 30 room temperature unless otherwise stated.) At this stage, an antigen retrieval step was performed on paraffin-embedded sections. These sections were microwaved in 0.01M citrate buffer for 20 min followed by cooling in water. All sections were then incubated for 30 min, with 10% normal serum from the species that the secondary antibody was raised in. Subsequently, sections were incubated with the 5-$HT_{2B}$ receptor antibody (1–2 mg/ml in PBS) for 16 h–72 h, at 4° C. Control sections were incubated with PBS alone or mouse $IgG_1$ at 1–2 mg/ml. Unless otherwise stated, sections were then washed (2×5 min) and incubated with biotinylated anti-mouse IgG (1:300 dilution; Amersham) for 30 min, followed by washing (2×5 min) and incubation with streptavidin-biotin conjugated to horse-radish peroxidase (1:600 dilution; Amersham) for 30 min. Subsequently, sections were incubated with 3', 3-diaminobenzidine tetrachloride (0.025% w/v)/$H_2O_2$ (0.02% v/v) in 0.05M Tris buffer (pH 7.6) for 5 min, followed by washing in distilled water. Some sections were counterstained in Mayer's haematoxylin (1 min). Sections were then dehydrated with xylene and coverslipped with DPX mountant (BDH Laboratories). Immunostained sections were viewed with a Zeiss Axioplan2 microscope.

Results

Dot blotting: The 5-$HT_{2B}$-like protein was detected in most of the 82 human tissue samples, but was highly abundant in extracts from both the urinary and gastrointestinal tracts.

Western Blotting: To confirm the presence and abundance of 5-$HT_{2B}$-like receptor protein in the samples as determined by dot-blotting, all 84 protein extracts were resolved by traditional SDS polyacrylamide gel electrophoresis and analysed by Western Blotting. The techniques allowed confirmation of the presence and abundance of 5-$HT_{2B}$-like protein, and also determination of the molecular weight of the receptor protein. There was a highly significant correlation ($P<0.001$; $r=0.721$) between protein quantification using the two blotting methods. The Western blotting confirmed the presence or absence of 5-$HT_{2B}$-like receptor protein in all samples. This included extractws from both the urinary and gastrointestinal tracts.

The molecular mass of the of 5-$HT_{2B}$-like receptor was found to be about 80,000 Da using information gained from FITC-labelled standard protein run alongside the protein extracts. In some samples, a lowered molecular mass protein species was present 5 with a molecular weight of approximately 60,000 Da. This is either degraded 5-$HT_{2B}$-like receptor species or a related protein recognised by the antibody.

Immunocytochemistry

Figure 3:
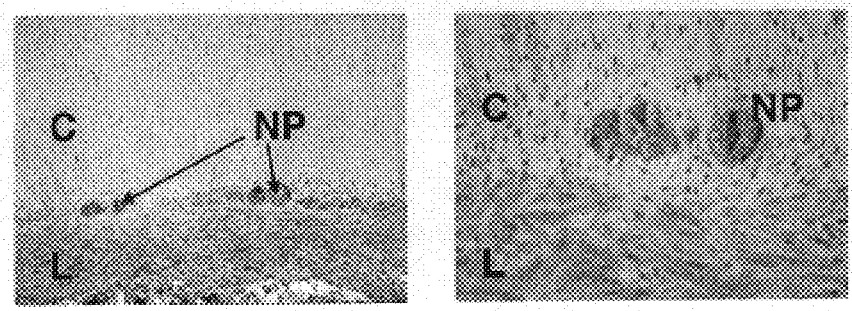
FIG. 3 shows $5\text{-}HT_{2B}$ receptor immunoreactivity in the human colon. In the muscularis externa, immunoreactivity was predominantly localised to the longitudinal (L) and circular (C) muscle cells (MC) and the myenteric nerve plexuses (NP).
Figure 4:
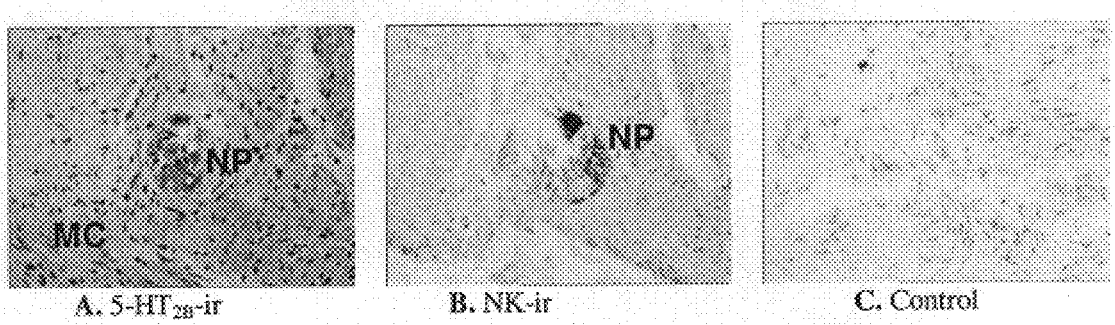
FIG. 4 shows irmunoreactivity of adjacent human colonic sections to (A) $5\text{-}HT_{2B}$ (B) Neurofilament 68 and (C) control IgG1 antibodies.

In the gastrointestinal tract, 5-$HT_{2B}$ receptor localisation was studied in human colon. In sections of human colon, 5-$HT_{2B}$ receptor-like immunoreactivity (5-$HT_{2B}$R-ir) was observed in several cell types. In the muscularis externa, moderate 5-$HT_{2B}$R-ir was seen in the circular (C) and longitudinal (L) muscle layers, while moderate to strong staining was observed in putative myenteric nerve plexuses (MP) lying between the two muscle layers (FIG. 3). Localisation of 5-$HT_{2B}$R-ir to the myenteric plexus was confirmed by immunolabelling of adjacent sections with the 5-$HT_{2B}$ receptor antibody (FIG. 4A), a neuronal marker antibody, neurofilament 68 (FIG. 4B), or the control IgG1 antibody (FIG. 4C).

Summary

Dot blot and Western Blot analysis has provided a detailed protein expression profile of the ~80 KDa 5$HT_{2B}$ a receptor protein throughout the human body. These data have demonstrated highly abundant expression of the 5-$HT_{2B}$ receptor protein expression within the urinary and gastrointestinal tracts, and within the lung parenchyma, cerebral artery, stomach fundus smooth muscle, uterus and prostate. In detailed immunocytochemical studies of the human colon and ileum, 5-$HT_{2B}$ receptor immmunoreactivity (5-$HT_{2B}$-ir) was observed in both the longitudinal and circular smooth muscle layers within the muscularis externa, and in the myenteric nerve plexuses lying between these two muscle layers.

Pharmacology

Sections of human colon were cut open along its longitudinal axis. The section was pinned out flat and the mucosa carefully removed using sharp dissecting scissors. Once the mucosa was removed, the section was turned over to reveal the three taenia coli (taenia mesencolica, taenia omentalis and taenia libera) and the muscle bands that lie between them. Longitudinal suscle strips (2 mm of wide by 20 mm long) were then cut from the tissue between the taenia cwli anid suspended between stainless steel hooks in organ chambers containing oxygenated (95% $O_2$/5% $CO_2$) Krebs solution at 37° C. The composition of the Krebs solution was as follows: NaCl (118.2mM), KCl (4.69 mM), $MgSO_4$, $7H_2O$ (1.18 mM), $KH_2PO_4$ (1.19 mM), glucose (11.1 mM), $NaHCO_3$ (25.0 mN), $CaCl_2.6H_2O$ (2.5 mM). Tissues were placed under a tension equivalent to 10 mN and left to equilibrate for a period of at least 60 minutes.

Responses were recorded using isometric transducers coupled to an Apple Macintosh computer via a MacLab interface. After 60 minutes, the longitudinal muscle sections of the human colon were stimulated electrically (submaximal voltage and frequency with 60s between successive stimulations) using parallel platinum wire electrodes and a Multistim D330 pulse stimulator. Upon electrical stimulation, the strips of human colon longitudinal smooth muscle responded with a rapid contraction.

Once the response to electrical stimulation had stabilised (stimulated responses differed by no more than 10%), the strips were exposed to increasing concentrations of 5-HT (or 5-HT receptor agonists), in the absence or presence of selective receptor antagonists.

Results

Electrical stimulation (15V, Ims pulse width, at submaximal frequency for 10 s every 60 s) causes highly reproducible, transient, contractile responses of isolated preparations of colon smooth muscle. the responses are inhibited by either tetrodotoxin or by atropine, indicating that they are neuronal in nature, and they involve (at least in part) cholinergic neurotransmission.

Figure 2:
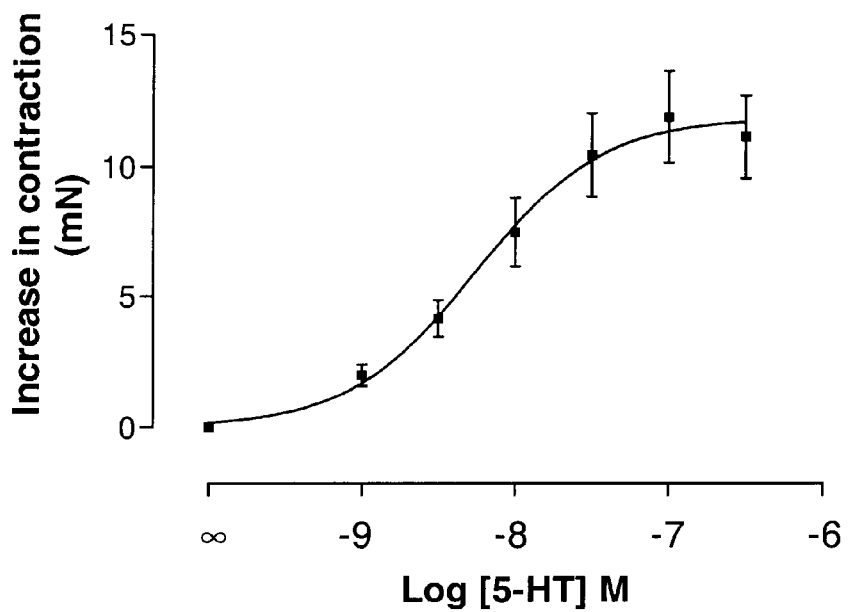
FIG. 2 shows the effect of 5-HT in colon smooth muscle. Figure shows mean concentration-effect curve to 5-HT, with data expressed as increase in contractility (mN) over basal EFS-induced contractions. Data are given as mean±s.e.mean for n=49 donors, and have been fitted to the Hill equation according to a 3 parameter curve fit.

Application of 5-HT, and a selection of 5-HT receptor agonists, has been shown to produce a concentration-dependent potentiation of the contractile response to electrical stimulation (FIGS. 1 and 2). The order of agonist potency would appear to implicate a receptor of the $5-HT_2$ family (Table 2), since the profile for the various agonists in colon matches most closely that observed for $5-HT_{2B}$ receptors.

The effects of various selective 5-HT receptor antagonists have also been tested, the antagonists caused a rightward shift of the concentration-response curve to 5-HT, and the profile generated corresponds to a receptor of the $5-HT_{2B}$ receptor class (Table 3).

TABLE 2

| Agonist | Colon | $5-HT_{2A}$ | $5-HT_{2B}$ | $5-HT_{2C}$ | $5-HT_4$ |
| --- | --- | --- | --- | --- | --- |
| Alpha-Me5-HT | 8.5 ± 0.1 | NA | 8.4 | NA | 6.2 |
| 5-HT | 8.2 ± 0.1 | 7.4 | 8.1 | 8.5 | 6.7 |
| 2-Me-5-HT | 7.0 ± 0.4 | NA | 6.7 | NA | 6.0 |

TABLE 2-continued

| Agonist | Colon | $5-HT_{2A}$ | $5-HT_{2B}$ | $5-HT_{2C}$ | $5-HT_4$ |
| --- | --- | --- | --- | --- | --- |
| 5-MeOT | 6.8 ± 0.2 | NA | 7.6 | NA | 6.2 |
| Cisapride | 5.8 ± 0.3 | NA | NA | NA | 5.5 |

Table 2. Potencies of some selective receptor agonists at the 5-HT receptor in human colon longitudinal muscle. Table shows he mean $pEC_{50}$ for agonists at the 5-HT receptor in colon (mean±s.e.mean for at least 3 donors) and also at human $5-HT_{2A, 2B, 2C}$ and $5-HT_4$ receptors, whereby all data are for human 5-HT receptors. NA indicates data are not available at the human receptor.

TABLE 3

| Antagonist | Colon | $5-HT_{2A}$ | $5-HT_{2B}$ | $5-HT_{2C}$ | $5-HT_4$ |
| --- | --- | --- | --- | --- | --- |
| RS 127445 | 9.4 ± 0.4 | 6.3# | 9.5# | 6.4* | NA |
| SB 206553 | 8.5 ± 0.1 | 6.0# | 9.0* | 7.9–9.0# | NA |
| Rauwolscine | 7.9 ± 0.2 | 6.6# | 7.0–7.8# | 5.8# | NA |
| Yohimbine | 7.5 ± 0.2 | 5.3# | 8.0* | <5.0 | NA |
| Methiothepin | 7.5 ± 0.3 | NA | 8.1# | NA | <6.0* |
| Cisapride | 7.1 ± 0.1 | 8.0# | 7.2# | 6.3# | NA |
| SB 204741 | 6.8 ± 0.2 | <5.0* | 7.0* | <6.0# | <5.0 |
| SB 242084 | 6.3 ± 0.2 | 6.8# | 7.0# | <6.0# | <5.0# |
| Ketanserin | 8.1 ± 0.2 | 8.6* | <6.0* | 6.8* | 4.7* |
| Methysergide | NSA at −9 M | 8.4* | 9.6* | 8.9* | <5.0* |

Table 3. Affinities of some selective receptor antagonists at the 5-HT receptor in human colon longitudinal muscle.

Table 3 shows the mean $pK_B$ or $pA_2$ for antagonists* or from binding data#, at the 5-HT receptor in colon and also at human $5-HT_{2A, 2B, 2C}$ and $5-HT_4$ receptors, whereby all data are for human 5-HT receptors. In colon, values given are $pK_B$ estimates, where antagonists were tested over at least 3 concentrations, except methysergide and methiothepin which were each tested at a single concentration each. All data were obtained in at least 3 donors. NA indicates data are not available at the human receptor, NSA indicates non-surmountable antagonism.

In summary, the agonist and antagonist profile of the receptor in human colon which mediates 5-HT-induced potentiation of the neuronal response to electrical stimulation corresponds to a receptor of the $5-HT_{2B}$ receptor sub-type. This shows for the first time that an antagonist of this receptor would counteract the effects of 5-HT in the human colon and would represent an effective treatment for IBS. pKB is calculated as described above; $pA_2$ is defined as the negative logarithm of the molar concentration of antagonist which would produce a 2-fold shift of the concentration-response curve for an agonist, At equilibrium, and assuming the antagonist is competitive, pA2 and pKB should be equal.

Therapeutic Mechanism

Physiological and pharmacological studies have indicated that 5-hydroxytryptamine (5-HT) may play a pivotal role in mediating sensory and reflex responses in the gastrointestinal tract of various species, including man (Read & Gwee, 1994). Administration of the 5-HT precursor, 5-hydroxytryptophan, has been shown to mimic the symptoms of IBS, and increased levels of 5-HT and its metabolites have been detected in plasma of patients suffering from IBS.

The nature of neuronal control of human intestinal motility is only partially elucidated. 5-HT has been reported to induce both excitatory and inhibitory responses throughout the human gastrointestinal tract (Misiewicz et al., 1966; Costal & Naylor, 1990). The nature of the receptors mediating these responses have not been well characterised. Extrapolating from animal data, we would expect 5-$HT_3$ and/or 5-$HT_4$ receptors to be implicated in these effects. However, little evidence has been found to support a role for such receptors in human gastrointestinal reflexes.

In the present invention, a receptor site (5-$HT_{2B}$) has been identified which is located in two key areas of the human gastrointestinal tract—1. neurones within the sub-mucous & myenteric plexus, and 2. smooth muscle. These data, along with certain functional evidence, have led the present inventors to develop a hypothesis in which the 5-$HT_{2B}$ receptor plays a key role in the initiation and maintenance of the symptomatically complex phenotype of irritable bowel syndrome (IBS).

Thus it is believed that the 5-$HT_{2B}$ receptor is located on neurones of the myenteric plexus and modulates the activity of these neurones, and that pathological increases in the levels of endogenous 5-HT causes 'misfiring' of the enteric reflexes which are essential for coordinated gastrointestinal motility and peristalsis. Finally, immunocytochemical and functional data indicate the presence of 5-$HT_{2B}$ receptors mediating gastrointestinal smooth muscle spasm in response to elevated levels of endogenous 5-HT.

The use of a 5-$HT_{2B}$ receptor antagonist will thus increase the activation threshold for neuronal and muscular 5-$HT_{2B}$ receptors, by endogenous 5-HT. This would result in a reduction of neuronal misfiring and muscular spasm, allowing 'normal', co-ordinated peristaltic activity to be restored. In a novel, in vitro preparation of human colon, 5-$HT_{2B}$ receptors are activated by low (nM) concentrations of 5-HT which mediates a substantial potentiation in the magnitude of electrically stimulated contractions. It is believed that activation of these 5-$HT_{2B}$ receptors is upstream of a chain of events which leads to the stimulation of sensory afferents leading to the pain of IBS.

Thus the present data show for the first time direct evidence to support the use of 5-$HT_{2B}$ antagonists in the treatment of IBS.

REFERENCES

Audia, J. E., Evard, D. A., Murdoch, G. R., Droste, J. J., Nissen, J. S., Schenck, K. W., Fludzinski, P., Lucaites, V. L., Nelson, D. L. & Cohen, M. L. (1996) Potent, selective tetrahydro-beta-carboline antagonists of the serotonin$_{2B}$ (5-$HT_{2B}$) contractile receptor in the rat stomach fundus. J Med. Chem., 39, 2773–2780.

Blondel, O., Gastineau, M., Dahmoune, Y., Langlois, M & Fischmeister, R. (1998) Cloning, expression, and pharmacology of four human 5-hydroxytryptamine 4 receptor isoforms produced by alternative splicing in the carboxy terminus. J. Neurochem., 70(6), 2252–2261.

Bonhaus, D. W., Eglen, R. M., Martin, G. R., Flippin, L. A., Greenhouse, R. J., Jaime, S., Rocha, C., Dawson, M, VanNatta, N., Chang, L. K., Pulido-Rios, T., & Webber, A. (1999) RS-127445, a novel, selective 5-HT receptorantagonist, inhibits neurogenic inflammatory responses in rat dura mater. British Pharmacological Society; 167.

Bonhaus D. W., Flippin L. A., Greenhouse R. J., Jaime S., Rocha C., Dawson M., Van Natta K., Chang L. K., Pulido-Rios T., Webber A., Leung E., Eglen R. M. & Martin G. R. (1999). RS-127445: a selective, high affinity, orally bioavailable 5-$HT_{2B}$ receptor antagonist. Br J Pharmacol., 127(5):1075–82.

Borman, R. A. & Burleigh, D. E. (1993). Evidence for the involvement of a 5-$HT_4$ receptor in the secretory response of human small intestine to 5-HT. Br. J. Pharmacol., 110, 927–928.

Briejer M R, Mathis C, Schuurkes J A (1997) 5-HT receptor types in the rat ileum longitudinal muscle: focus on 5-$HT_2$ receptors mediating contraction. Neurogastroenterol Motil 9; 231–7.

Camilleri M., Mayer E. A., Drossman D. A., Heath A., Dukes G. E., McSorley D., Kong S., Mangel A. W. & Northcutt A. R. (1999) Improvement in pain and bowel function in female irritable bowel patients with alosetron, a 5-HT receptor antagonist. Aliment. Pharmaco.l Ther., 13(9), 1149–1159.

Costall, B. & Naylor, R. J. (1990) 5-hydroxytryptamine: new receptors and novel drugs for gastrointestinal motor disorders. Scand. J. Gastroenterol., 25, 769–787.

Emmanuel, A. V., Kanrn, M. A., Roy, A. J. & Antonelli, K. (1998) Effect of a novel prokinetic drug, R093877, on gastrointestinal transit in healthy volunteers. Gut, 42(4), 511–516.

McLean, P. G., Coupar, I. M. & Molenaar, P. (1993) Effect of the novel 5-$HT_4$ receptor agonist DAU 6236 in human colon. Med. J. Australia., 159, 834.

Misiewicz, J. J., Waller, S. L. & Eisner, M. (1966) Motor responses of human gastrointestinal tract to 5-hydroxytryptamine in vivo and in vitro. Gut., 7, 208.

Porter, R. H. P., Benwell, K. R., Lamb, H., Malcolm, C. S., Allen, N. H., Revell, D. F., Adamsr D. R. & Sheardown, M. J. (1999) Functional characterization of agonists at recombinant human 5- $HT_{2A}$, 5-$HT_{2B}$ and 5-$HT_{2C}$ receptors in CHO-K1 cells. Br. J. Pharmacol., 128, 13–20.

Prins N. H., Briejer M. R. & Schuurkes J. A. (1997) Characterization of the contraction to 5-HT in the canine colon longitudinal muscle. Br. J. Pharmacol., 120(4):714–20.

Prins, N. H., Briejer, M. R. & Schuurkes, J. A. (1997) Characterization of the contraction to 5-HT in the canine colon longitudinal muscle. Br J Pharmacol 120, 714–20.

Read, N. W. & Gwee, K-A. (1994) The importance of 5-hyroxytryptamine receptors in the gut. Pharmacol. Ther., 62, 159–173.

Thompson, W. G., Longstreth, G. F., Drossman, D. A., Heaton, K. W., Irvine, E. J. & Muller-Lissner. S. A, (1999) Functional bowel disorders and functional abdominal pain. Gut, 45(II), II43–II47.

Watts, S. W. & Fink, G. D. (1999) 5-$HT_{2B}$-receptor antagonist LY-272015 is antihypertensive in DOCA-salt-hypertensive rats. A M. J. Physiol. 276; H944–52.

Schmidt A. W. & Peroutka S. J. (1989) Three-dimensional steric molecular modelling of the 5-hydroxytryptamine3 receptor pharmacophore. Mol. Pharmacol. 36(4):505–11.

We claim:

1. An assay to determine whether or not a compound is capable of antagonising 5-$HT_{2B}$ receptor activity, which assay comprises determining whether or not said compound is capable of antagonising said activity in the human colon.

2. The assay of claim 1 which comprises:
   providing a section of human colon;
   placing said section under tension;
   electrically stimulating said section in the presence of a potential 5-$HT_{2B}$ receptor antagonist; and
   observing whether said potential 5-$HT_{2B}$ receptor antagonist is capable of antagonising the 5-HT induced potentiation of electrically stimulated contractions of said human colon.

3. The assay of claim 1 which further comprises selecting a compound having antagonist activity and formulating said compound for administration to the colon.

* * * * *